United States Patent
Altmann et al.

(10) Patent No.: US 7,604,601 B2
(45) Date of Patent: Oct. 20, 2009

(54) DISPLAY OF CATHETER TIP WITH BEAM DIRECTION FOR ULTRASOUND SYSTEM

(75) Inventors: Andres Claudio Altmann, Haifa (IL); Assaf Govari, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 436 days.

(21) Appl. No.: 11/115,013

(22) Filed: Apr. 26, 2005

(65) Prior Publication Data

US 2006/0253032 A1    Nov. 9, 2006

(51) Int. Cl.
*A61B 8/14*    (2006.01)
(52) U.S. Cl. .......................... 600/463; 600/437; 600/466
(58) Field of Classification Search .......... 600/437–466
See application file for complete search history.

(56) References Cited

U.S. PATENT DOCUMENTS

| | | | |
|---|---|---|---|
| 4,751,643 A | 6/1988 | Lorensen et al. | |
| 4,791,567 A | 12/1988 | Cline et al. | |
| 5,391,199 A | 2/1995 | Ben-Haim | |
| 5,568,384 A | 10/1996 | Robb et al. | |
| 5,738,096 A | 4/1998 | Ben-Haim | |
| 5,797,849 A | 8/1998 | Vesely et al. | |
| 5,846,205 A | 12/1998 | Curley et al. | |
| 5,848,969 A | 12/1998 | Panescu et al. | |
| 5,876,345 A * | 3/1999 | Eaton et al. ................. | 600/466 |

(Continued)

FOREIGN PATENT DOCUMENTS

EP    0 961 135 B1    12/1999

(Continued)

OTHER PUBLICATIONS

McInerney et al. Deformable Models in Medical Image Analysis: A Survey, Medical Image Analysis (I:2), Jun. 1996, pp. 91-108 (Abstract).

(Continued)

*Primary Examiner*—Long V Le
*Assistant Examiner*—Sanjay Cattungal

(57) ABSTRACT

A medical imaging system for imaging a patient's body includes a catheter having a position sensor and an ultrasonic imaging sensor wherein the position sensor transmits electrical signals indicative of positional information of a portion of the catheter in a patient's body and the ultrasonic imaging sensor transmits ultrasonic energy at a target in the patient's body, receives ultrasonic echoes reflected from the target in the patient's body and transmits signals relating to the ultrasonic echoes reflected from the target in the patient's body. A positioning processor is operatively connected to the catheter for determining positional information of the portion of the catheter based on the electrical signals transmitted by the position sensor. The system also includes a display and an image processor operatively connected to the catheter, the positioning processor and the display. The image processor displays on the display a catheter icon in a same orientation as an orientation of the portion of the catheter in the patient's body based on positional information derived from the position sensor. The image processor also generates an ultrasonic image of the target based on the signals transmitted by the ultrasonic sensor and depicts in real-time the generated ultrasound image on a display in a same orientation as the orientation of the portion of the catheter in the patient's body based on positional information derived from the position sensor.

11 Claims, 9 Drawing Sheets

U.S. PATENT DOCUMENTS

| | | | |
|---|---|---|---|
| 5,904,651 A | 5/1999 | Swanson et al. | |
| 6,004,269 A | 12/1999 | Crowley et al. | |
| 6,049,622 A | 4/2000 | Robb et al. | |
| 6,059,731 A | 5/2000 | Seward et al. | |
| 6,066,096 A | 5/2000 | Smith et al. | |
| 6,171,248 B1 * | 1/2001 | Hossack et al. | 600/459 |
| 6,226,542 B1 | 5/2001 | Reisfeld | |
| 6,226,546 B1 | 5/2001 | Evans | |
| 6,228,032 B1 | 5/2001 | Eaton et al. | |
| 6,332,089 B1 | 12/2001 | Acker et al. | |
| 6,618,612 B1 * | 9/2003 | Acker et al. | 600/424 |
| 6,690,963 B2 | 2/2004 | Ben-Haim et al. | |
| 6,716,166 B2 * | 4/2004 | Govari | 600/437 |
| 6,773,402 B2 * | 8/2004 | Govari et al. | 600/459 |
| 2002/0065455 A1 | 5/2002 | Ben-Haim et al. | |
| 2003/0065265 A1 | 4/2003 | Jackson et al. | |
| 2003/0199748 A1 | 10/2003 | Camus et al. | |
| 2003/0231789 A1 | 12/2003 | Willis et al. | |
| 2004/0068178 A1 | 4/2004 | Govari | |
| 2004/0147920 A1 | 7/2004 | Keidar | |

FOREIGN PATENT DOCUMENTS

| | | |
|---|---|---|
| EP | 1 354 557 A1 | 10/2003 |
| EP | 1 504 721 A1 | 2/2005 |
| EP | 1 815 797 A1 | 8/2007 |
| WO | WO 96/25881 A1 | 8/1996 |
| WO | WO 98/46139 A1 | 10/1998 |
| WO | WO 99/05971 A1 | 2/1999 |
| WO | WO 99/55233 A1 | 11/1999 |
| WO | WO 00/07501 A1 | 2/2000 |
| WO | WO 00/19908 A1 | 4/2000 |

OTHER PUBLICATIONS

Neubauer et al. Analysis of Four-Dimensional Cardiac Data Sets Using Skeleton-Based Segmentation, The 11$^{th}$ International Conference in Central Europe on Computer Graphics, Visualization and Computer Vision, University of West Bohemia, Pizen, Czech Republic, Feb. 2003.

McInerney et al. Deformable Models in Medical Image Analysis: A Survey, Medical Image Analysis (I:2), Jun. 1996, pp. 91-108.

European Search Report EP 06 25 2217 dated Jan. 25, 2008.

* cited by examiner

DISPLAY OF CATHETER TIP WITH BEAM DIRECTION FOR ULTRASOUND SYSTEM

FIELD OF THE INVENTION

The present invention relates generally to medical imaging systems, and particularly to methods and systems for constructing three-dimensional organ models from multiple ultrasonic images.

BACKGROUND OF THE INVENTION

Methods for three-dimensional (3-D) mapping of the endocardium (i.e., the inner surfaces of the heart) are known in the art. For example, U.S. Pat. No. 5,738,096, whose disclosure is incorporated herein by reference, describes a method for constructing a map of the heart. An invasive probe is brought into contact with multiple locations on the wall of the heart. The position of the invasive probe is determined for each location, and the positions are combined to form a structural map of at least a portion of the heart.

In some systems, such as the one described by U.S. Pat. No. 5,738,096 cited above, additional physiological properties, as well as local electrical activity on the surface of the heart, are also acquired by the catheter. A corresponding map incorporates the acquired local information.

Some systems use hybrid catheters that incorporate position sensing. For example, U.S. Pat. No. 6,690,963, whose disclosure is incorporated herein by reference, describes a locating system for determining the location and orientation of an invasive medical instrument.

A catheter with acoustic transducers may be used for non-contact imaging of the endocardium. For example, U.S. Pat. Nos. 6,716,166 and 6,773,402, whose disclosures are also incorporated herein by reference, describe a system for 3-D mapping and geometrical reconstruction of body cavities, particularly of the heart. The system uses a cardiac catheter comprising a plurality of acoustic transducers. The transducers emit ultrasonic waves that are reflected from the surface of the cavity and are received again by the transducers. The distance from each of the transducers to a point or area on the surface opposite the transducer is determined, and the distance measurements are combined to reconstruct the 3-D shape of the surface. The catheter also comprises position sensors, which are used to determine position and orientation coordinates of the catheter within the heart.

U.S. Pat. No. 5,846,205, whose disclosure is incorporated herein by reference, describes a phased-array ultrasonic transducer assembly that includes a catheter. An end portion is mounted to the catheter around a transducer array, and the end portion defines an acoustic window, which is essentially non-focusing to ultrasonic energy passing therethrough. Because the acoustic window is non-focusing, the inventors claim that a relatively small radius of curvature can be used on the radial outer surface of this window.

U.S. Pat. No. 6,066,096, whose disclosure is incorporated herein by reference, describes an imaging probe for volumetric intraluminal ultrasound imaging. The probe, configured to be placed inside a patient body, includes an elongated body having proximal and distal ends. An ultrasonic transducer phased array is connected to and positioned on the distal end of the elongated body. The ultrasonic transducer phased array is positioned to emit and receive ultrasonic energy for volumetric forward scanning from the distal end of the elongated body. The ultrasonic transducer phased array includes a plurality of sites occupied by ultrasonic transducer elements. At least one ultrasonic transducer element is absent from at least one of the sites, thereby defining an interstitial site. A tool is positioned at the interstitial site. In particular, the tool can be a fiber optic lead, a suction tool, a guide wire, an electrophysiological electrode, or an ablation electrode.

U.S. Pat. No. 6,059,731, whose disclosure is incorporated herein by reference, describes a simultaneous side-and-end viewing ultrasound imaging catheter system. The system includes at least one side array and at least one end array. Each of the arrays has at least one row of ultrasonic transducer elements. The elements are operable as a single ultrasound transducer and are phased to produce different views.

U.S. Pat. No. 5,904,651, whose disclosure is incorporated herein by reference, describes a catheter tube that carries an imaging element for visualizing tissue. The catheter tube also carries a support structure, which extends beyond the imaging element, for contacting surrounding tissue away from the imaging element. The support element stabilizes the imaging element, while the imaging element visualizes tissue in the interior body region. The support structure also carries a diagnostic or therapeutic component to contact surrounding tissue.

U.S. Pat. No. 5,876,345, whose disclosure is incorporated herein by reference, describes an ultrasonic catheter for two-dimensional (2-D) imaging or 3-D reconstruction. The ultrasonic catheter includes at least two ultrasonic arrays having good near and far field resolutions. The catheter provides an outline of a heart chamber, in order to assist in interpreting images obtained by the catheter.

U.S. Pat. No. 6,228,032, whose disclosure is incorporated herein by reference, describes a steering mechanism and steering line for a catheter-mounted phased linear array of ultrasonic transducer elements.

U.S. Pat. No. 6,226,546, whose disclosure is incorporated herein by reference, describes a catheter location system for generating a 3-D map of a part of a human body, from which a position of the catheter may be determined. A plurality of acoustic transducers is disposed about the catheter head at predetermined locations. Acoustic signals are generated by the acoustic transducers acting as sources. A signal processing unit generates the 3-D map responsive to signals received by the acoustic transducers acting as acoustic receivers.

U.S. Pat. No. 6,171,248, whose disclosure is incorporated herein by reference, describes an ultrasonic probe for 2-D imaging or 3-D reconstruction. The patent describes an ultrasonic probe that includes at least two ultrasonic arrays. The probe allows 3-D images to be constructed and examined.

Several methods are known in the art for non-contact reconstruction of the endocardial surface using intracardial ultrasonic imaging. For example, PCT Patent Publication WO 00/19908, whose disclosure is incorporated herein by reference, describes a steerable transducer array for intracardial ultrasonic imaging. The array forms an ultrasonic beam, which is steered in a desired direction by an active aperture. U.S. Pat. No. 6,004,269, whose disclosure is also incorporated herein by reference, describes an acoustic imaging system based on an ultrasound device that is incorporated into a catheter. The ultrasound device directs ultrasonic signals toward an internal structure in the heart to create an ultrasonic image. PCT Patent Publications WO 99/05971 and WO 00/07501, whose disclosures are incorporated herein by reference, describe the use of ultrasound transducers on a reference catheter to locate ultrasound transducers on other catheters (e.g., mapping or ablation catheters) which are brought into contact with the endocardium.

Further examples of intracardial ultrasonic imaging are presented in U.S. Pat. No. 5,848,969, whose disclosure is incorporated herein by reference. This publication describes systems and methods for visualizing interior tissue regions using expandable imaging structures.

PCT Patent Publication WO 99/55233, whose disclosure is incorporated herein by reference, describes a method for delineating a 3-D surface of a patient's heart. A 3-D mesh model is developed using training data, to serve as an archetypal shape for a population of patient hearts. Multiple ultrasound images of the patient's heart are taken in different image planes. Anatomical locations are manually identified in each of the images. The mesh model is rigidly aligned with the images, in respect to the predefined anatomical locations.

Other methods of contour extraction and 3-D modeling using ultrasonic images are described in European Patent Application EP 0961135, whose disclosure is incorporated herein by reference. As another example, PCT Patent Publication WO 98/46139, whose disclosure is also incorporated herein by reference, describes a method for combining Doppler and B-mode ultrasonic image signals into a single image using a modulated nonlinear mapping function.

U.S. Pat. No. 5,797,849, whose disclosure is incorporated herein by reference, describes a method for carrying out a medical procedure using a 3-D tracking and imaging system. A surgical instrument is inserted into a patient body. The position of the surgical instrument is tracked as it moves through a bodily structure. The location of the surgical instrument relative to its immediate surroundings is displayed to improve a physician's ability to precisely position the surgical instrument.

U.S. Pat. No. 5,391,199, whose disclosure is incorporated herein by reference, describes a method for ablating a portion of an organ or bodily structure of a patient. The method includes obtaining a perspective image of an organ or structure to be mapped, and advancing one or more catheters to sites adjacent to or within the organ or structure. The location of each catheter distal tip is sensed using a non-ionizing field. At the distal tip of one or more catheters, local information of the organ or structure is sensed, and the sensed information is processed to create one or more data points. The data points are superimposed on a perspective image of the organ or structure, to facilitate the ablating of a portion of the organ or structure.

Some medical imaging systems apply methods for reconstructing 3-D models, based on acquired imaging information. For example, U.S. Pat. No. 5,568,384, whose disclosure is incorporated herein by reference, describes a method for synthesizing 3-D multimodality image sets into a single composite image. Surfaces are extracted from two or more different images and matched using semi-automatic segmentation techniques.

U.S. Pat. No. 6,226,542, whose disclosure is incorporated herein by reference, describes a method for 3-D reconstruction of intrabody organs. A processor reconstructs a 3-D map of a volume or cavity in a patient's body from a plurality of sampled points on the volume whose position coordinates have been determined. Reconstruction of a surface is based on a limited number of sampled points.

U.S. Pat. Nos. 4,751,643 and 4,791,567, whose disclosures are incorporated herein by reference, describe a method for determining connected substructures within a body. 3-D regions exhibiting the same tissue type are similarly labeled. Using the label information, all similarly labeled connected data points are determined.

Some systems use image processing methods for analyzing and modeling body tissues and organs based on information acquired by imaging. One such technique is described by McInerney and Terzopoulos in "Deformable Models in Medical Image Analysis: A Survey," Medical Image Analysis, (1:2), June 1996, pages 91-108, which is incorporated herein by reference. The authors describe a computer-assisted medical image analysis technique for segmenting, matching, and tracking anatomic structures by exploiting (bottom-up) constraints derived from the image data together with (top-down) a priori knowledge about the location, size, and shape of these structures.

Another analysis technique is described by Neubauer and Wegenkittl in "Analysis of Four-Dimensional Cardiac Data Sets Using Skeleton-Based Segmentation," the 11$^{th}$ International Conference in Central Europe on Computer Graphics, Visualization and Computer Vision, University of West Bohemia, Plzen, Czech Republic, February 2003, which is incorporated herein by reference. The authors describe a computer-aided method for segmenting parts of the heart from a sequence of cardiac CT (Computerized Tomography) images, taken at a number of time points over the cardiac cycle.

SUMMARY OF THE INVENTION

Three-dimensional images of the heart are useful in many catheter-based diagnostic and therapeutic applications. Real-time imaging improves physician performance and enables even relatively inexperienced physicians to perform complex is surgical procedures more easily. 3-D imaging also helps to reduce the time needed to perform some surgical procedures. Additionally, 3-D ultrasonic images can be used in planning complex procedures and catheter maneuvers.

Embodiments of the present invention provide improved methods and systems for performing 3-D cardiac imaging. A probe that comprises an array of ultrasound transducers and a position sensor is used to image a target organ or structure in the patient's body. In one embodiment, the probe comprises a catheter, which is inserted into the patient's heart. The probe acquires multiple 2-D ultrasound images of the target organ and sends them to an image processor. For each image, location and orientation coordinates of the probe are measured using the position sensor.

A user of the system, typically a physician, examines the images on an interactive display. The user employs the display to manually mark (also referred to as "tagging") contours of interest that identify features of the organ, on one or more of the images. Additionally or alternatively, the contours are tagged automatically using a contour detection software. An image processor automatically identifies and reconstructs the corresponding contours in at least some of the remaining, untagged images. The image processor then constructs a 3-D structural model based on the multiple ultrasound images and the corresponding probe coordinates at which each of the images was captured, using the contours to segment the 3-D structures in the model.

In some embodiments, the contours comprise discrete points. The 3-D coordinate of each point is calculated using the position sensor information and the 2-D ultrasound image properties. The calculated positions are used to construct the 3-D model. The contours tagged by the physician may be projected and displayed on top of the 3-D model.

The disclosed methods thus provide an interactive tool for user-aided reconstruction of 3-D images of an internal body organ. These methods also provide a convenient, accurate way to define the anatomical surface onto which an electrical activity map (particularly in cardiac imaging applications) or a map or image of another kind is to be projected.

There is therefore provided, in accordance with an embodiment of the present invention, a method for modeling of an anatomical structure, including:

acquiring a plurality of ultrasonic images of the anatomical structure using an ultrasonic sensor, at a respective plurality of spatial positions of the ultrasonic sensor;

measuring location and orientation coordinates of the ultrasonic sensor at each of the plurality of spatial positions;

marking contours-of-interest that refer to features of the anatomical structure in one or more of the ultrasonic images; and constructing a three-dimensional (3-D) model of the anatomical structure based on the contours-of-interest and on the measured location and orientation coordinates.

In a disclosed embodiment, constructing the 3-D model includes automatically reconstructing the features in at least some of the ultrasonic images that were not marked, based on the marked contours-of-interest.

In another embodiment, the anatomical structure includes a heart, and acquiring the plurality of ultrasonic images includes inserting a catheter including the ultrasonic sensor into a first cardiac chamber and moving the catheter between the respective plurality of spatial positions within the chamber. Additionally or alternatively, constructing the 3-D model includes constructing the 3-D model of a target structure located outside the first cardiac chamber.

In yet another embodiment, acquiring the ultrasonic images and measuring the location and orientation coordinates includes synchronizing a timing of acquisition of the ultrasonic images and measurement of the location and orientation coordinates relative to a synchronizing signal including one of an electrocardiogram (ECG) signal, an internally-generated synchronization signal and an externally-supplied synchronization signal. Additionally or alternatively, synchronizing the timing and measurement includes synchronizing the measurement of at least one of a tissue characteristic, a temperature and a blood flow relative to the synchronization signal.

In still another embodiment, measuring the location and orientation coordinates includes generating fields in a vicinity of a position sensor associated with the ultrasonic sensor, sensing the fields at the position sensor, and calculating the location and orientation coordinates of the ultrasonic sensor responsively to the sensed fields. In some embodiments, generating the fields includes generating magnetic fields, and sensing the fields includes sensing the generated magnetic fields at the position sensor.

In another embodiment, measuring the location and orientation coordinates includes generating a field using a field generator associated with the ultrasonic sensor, sensing the field using one or more receiving sensors, and calculating the location and orientation coordinates of the ultrasonic sensor responsively to the sensed field. In some embodiments, generating the field includes generating a magnetic field, and sensing the field includes sensing the generated magnetic field at the one or more receiving sensors.

In an embodiment, automatically reconstructing the features includes accepting manual input including at least one of an approval, a deletion, a correction and a modification of at least part of the automatically reconstructed features.

In another embodiment, constructing the 3-D model includes generating at least one of a skeleton model and a surface model of a target structure of the anatomical structure and displaying the 3-D model to a user. Additionally or alternatively, generating the surface model includes overlaying at least one of an electrical activity map and a parametric map on the surface model.

In yet another embodiment, constructing the 3-D model includes overlaying information imported from one or more of a Magnetic Resonance Imaging (MRI) system, a Computerized Tomography (CT) system and an x-ray imaging system on the 3-D model. Additionally or alternatively, overlaying the information includes registering the imported information with a coordinate system of the 3-D model.

In still another embodiment, constructing the 3-D model includes defining one or more regions of interest in the 3-D model and projecting parts of the ultrasonic images that correspond to the one or more regions of interest on the 3-D model.

In an embodiment, acquiring the plurality of ultrasonic images includes scanning the anatomical structure using an extracorporeal ultrasonic probe including the ultrasonic sensor and moving the probe between the respective plurality of spatial positions.

There is additionally provided, in accordance with an embodiment of the present invention, a method for modeling of an anatomical structure, including:

acquiring an ultrasonic image of the anatomical structure using an ultrasonic sensor, at a spatial position of the ultrasonic sensor;

measuring location and orientation coordinates of the ultrasonic sensor at the spatial position;

marking contours-of-interest that refer to features of the anatomical structure in the ultrasonic image; and displaying at least part of the ultrasonic image and the contours-of-interest in a 3-D space based on the measured location and orientation coordinates.

There is also provided, in accordance with an embodiment of the present invention, a system for modeling of an anatomical structure, including:

a probe, including:
an ultrasonic sensor, which is configured to acquire a plurality of ultrasonic images of the anatomical structure at a respective plurality of spatial positions of the probe; and
a position sensor, which is configured to determine location and orientation coordinates of the ultrasonic sensor at each of the plurality of spatial positions;

an interactive display, which is coupled to display the ultrasonic images and to receive a manual input marking contours-of-interest that refer to features of the anatomical structure in one or more of the ultrasonic images; and a processor, which is coupled to receive the ultrasonic images and the measured location and orientation coordinates, to accept the manually-marked contours-of-interest and to construct a 3-D model of the anatomical structure based on the contours-of-interest and on the measured spatial positions.

There is further provided, in accordance with an embodiment of the present invention, a system for modeling of an anatomical structure, including:

a probe, including:
an ultrasonic sensor, which is configured to acquire an image of the anatomical structure at a respective spatial position of the probe; and
a position sensor, which is configured to determine location and orientation coordinates of the ultrasonic sensor at the spatial position;

a processor, which is coupled to receive the ultrasonic image and the measured location and orientation coordinates and to calculate a 3-D position of the ultrasonic image based on the measured location and orientation coordinates; and an interactive display, which is coupled to receive a manual input marking contours-of-interest that refer to features of the anatomical structure in the ultrasonic image and to display at least part of the ultrasonic image and the contours-of-interest in a 3-D space based on the calculated 3-D position of the ultrasonic image.

There is additionally provided, in accordance with an embodiment of the present invention, a computer software product for modeling of an anatomical structure, the product including a computer-readable medium, in which program instructions are stored, which instructions, when read by the computer, cause the computer to acquire a plurality of ultrasonic images of the anatomical structure using an ultrasonic sensor, at a respective plurality of spatial positions of the ultrasonic sensor, to measure location and orientation coordinates of the ultrasonic sensor at each of the plurality of spatial positions, to receive a manual input marking contours-of-interest that refer to features of the anatomical structure in one or more of the ultrasonic images and to construct a 3-D model of the anatomical structure based on the contours-of-interest and on the measured location and orientation coordinates.

There is also provided, in accordance with an embodiment of the present invention, a computer software product for modeling of an anatomical structure, the product including a computer-readable medium, in which program instructions are stored, which instructions, when read by the computer, cause the computer to acquire an ultrasonic image of the anatomical structure using an ultrasonic sensor, at a respective spatial position of the ultrasonic sensor, to measure location and orientation coordinates of the ultrasonic sensor at the spatial position, to mark contours-of-interest that refer to features of the anatomical structure in the ultrasonic image, and to display at least part of the ultrasonic image and the contours-of-interest in a 3-D space based on the measured location and orientation coordinates.

The present invention also is directed to a system for imaging a target in a patient's body wherein the system comprises:
  a pre-acquired image;
  a catheter comprising a position sensor and an ultrasonic imaging sensor, the position sensor transmitting electrical signals indicative of positional information of a portion of the catheter in the patient's body, and the ultrasonic imaging sensor transmitting ultrasonic energy at the target in the patient's body, receiving ultrasonic echoes reflected from the target in the patient's body and transmitting signals relating to the ultrasonic echoes reflected from the target in the patient's body;
  a positioning processor operatively connected to the catheter for determining positional information of the portion of the catheter based on the electrical signals transmitted by the position sensor;
  an image processor operatively connected to the catheter and the positioning processor, the image processor generating an ultrasonic image of the target based on the signals transmitted by the ultrasonic sensor and determining positional information for any pixel of the ultrasonic image of the target, the image processor registering the pre-acquired image with the ultrasonic image; and
  a display for displaying the registered pre-acquired image and ultrasonic image.

Another embodiment of the present invention is a method for imaging a target in a patient's body wherein the method comprises the steps of:
  providing a pre-acquired image of the target;
  placing a catheter comprising a position sensor and an ultrasonic imaging sensor in the patient's body and determining positional information of a portion of the catheter in the patient's body using the position sensor;
  generating an ultrasonic image of the target using the ultrasonic imaging sensor;
  determining positional information for any pixel of the ultrasonic image of the target and registering the pre-acquired image with the ultrasonic image; and
  displaying the registered pre-acquired image and ultrasonic image.

Another embodiment in accordance with the present invention is directed to a system for imaging a target in a patient's body wherein the system comprises:
  a pre-acquired image of the target;
  an electrophysiological map of the target;
  a catheter comprising a position sensor and an ultrasonic imaging sensor, the position sensor transmitting electrical signals indicative of positional information of a portion of the catheter in the patient's body, and the ultrasonic imaging sensor transmitting ultrasonic energy at the target in the patient's body, receiving ultrasonic echoes reflected from the target in the patient's body and transmitting signals relating to the ultrasonic echoes reflected from the target in the patient's body;
  a positioning processor operatively connected to the catheter for determining positional information of the portion of the catheter based on the electrical signals transmitted by the position sensor;
  an image processor operatively connected to the catheter and the positioning processor, the image processor generating an ultrasonic image of the target based on the signals transmitted by the ultrasonic sensor and determining positional information for any pixel of the ultrasonic image of the target, the image processor registering the pre-acquired image and the electrophysiological map with the ultrasonic image; and
  a display for displaying the registered pre-acquired image, electrophysiological map and ultrasonic image.

And, a further embodiment in accordance with the present invention is a system for imaging a target in a patient's body wherein the system comprises:
  a pre-acquired image of the target;
  a catheter comprising a position sensor, an ultrasonic imaging sensor and at least one electrode, the position sensor transmitting electrical signals indicative of positional information of a portion of the catheter in the patient's body, the ultrasonic imaging sensor transmitting ultrasonic energy at the target in the patient's body, receiving ultrasonic echoes reflected from the target in the patient's body and transmitting signals relating to the ultrasonic echoes reflected from the target in the patient's body and the at least one electrode acquiring electrical activity data-points of a surface of the target;
  a positioning processor operatively connected to the catheter for determining positional information of the portion of the catheter based on the electrical signals transmitted by the position sensor;
  an image processor operatively connected to the catheter and the positioning processor, the image processor generating an ultrasonic image of the target based on the signals transmitted by the ultrasonic sensor and determining positional information for any pixel of the ultrasonic image of the target and for the electrical activity data-points of the target, the image processor creating an electrophysiological map of the target based on the electrical activity data-points of the target and the positional information for the electrical activity data-points and registering the pre-acquired image and the electrophysiological map with the ultrasonic image; and a display for displaying the registered pre-acquired image, electrophysiological map and ultrasonic image.

Additionally, the present invention is also directed to a method for imaging a target in a patient's body, wherein the method comprises the steps of:

providing a pre-acquired image of the target;
providing an electrophysiological map of the target;
placing a catheter comprising a position sensor and an ultrasonic imaging sensor in the patient's body and determining positional information of a portion of the catheter in the patient's body using the position sensor;
generating an ultrasonic image of the target using the ultrasonic imaging sensor;
determining positional information for any pixel of the ultrasonic image of the target and registering the pre-acquired image and the electrophysiological map with the ultrasonic image; and
displaying the registered pre-acquired image, electrophysiological map and ultrasonic image.

Another embodiment according to the present invention is a method for imaging a target in a patient's body wherein the method comprises the steps of:

providing a pre-acquired image of the target;
placing a catheter comprising a position sensor, an ultrasonic imaging sensor and at least one electrode, in the patient's body and determining positional information of a portion of the catheter in the patient's body using the position sensor;
acquiring electrical activity data-points of a surface of the target using the at least one electrode;
generating an ultrasonic image of the target using the ultrasonic imaging sensor;
determining positional information for the electrical activity data-points of the surface of the target and generating an electrophysiological map of the target based on the electrical activity data-points and the positional information for the electrical activity data-points;
determining positional information for any pixel of the ultrasonic image of the target and registering the pre-acquired image and the electrophysiological map with the ultrasonic image; and
displaying the registered pre-acquired image, electrophysiological map and ultrasonic image.

Furthermore, the present invention is also directed to a medical imaging system for imaging a patient's body wherein the system comprises:

a catheter comprising a position sensor and an ultrasonic imaging sensor, the position sensor transmitting electrical signals indicative of positional information of a portion of the catheter in a patient's body and the ultrasonic imaging sensor transmitting ultrasonic energy at a target in the patient's body, receiving ultrasonic echoes reflected from the target in the patient's body and transmitting signals relating to the ultrasonic echoes reflected from the target in the patient's body;
a positioning processor operatively connected to the catheter for determining positional information of the portion of the catheter based on the electrical signals transmitted by the position sensor;
a display; and
an image processor operatively connected to the catheter, the positioning processor and the display, the image processor generating an ultrasonic image of the target based on the signals transmitted by the ultrasonic sensor and depicting in real-time the generated ultrasound image on a display in a same orientation as an orientation of the portion of the catheter in the patient's body based on positional information derived from the position sensor.

Moreover, the present invention is also directed to a medical imaging system for imaging a target in a patient's body wherein the system comprises:

a catheter comprising a position sensor and an ultrasonic imaging sensor, the position sensor transmitting electrical signals indicative of positional information of a portion of the catheter in a patient's body and the ultrasonic imaging sensor transmitting ultrasonic energy at a target in the patient's body, receiving ultrasonic echoes reflected from the target in the patient's body and transmitting signals relating to the ultrasonic echoes reflected from the target in the patient's body;
a positioning processor operatively connected to the catheter for determining positional information of the portion of the catheter based on the electrical signals transmitted by the position sensor;
a display; and
an image processor operatively connected to the catheter, the positioning processor and the display, the image processor generating a plurality of two-dimensional ultrasonic images of the target based on the signals transmitted by the ultrasonic sensor and reconstructing a three-dimensional model using the plurality of two-dimensional ultrasonic images and depicting a real-time two-dimensional ultrasonic image on the three-dimensional model on the display in a same orientation as an orientation of the portion of the catheter in the patient's body based on positional information derived from the position sensor.

Additionally, the present invention is also directed to a medical imaging system for imaging a target in a patient's body, wherein the system comprises:

a pre-acquired image;
a catheter comprising a position sensor and an ultrasonic imaging sensor, the position sensor transmitting electrical signals indicative of positional information of a portion of the catheter in a patient's body and the ultrasonic imaging sensor transmitting ultrasonic energy at a target in the patient's body, receiving ultrasonic echoes reflected from the target in the patient's body and transmitting signals relating to the ultrasonic echoes reflected from the target in the patient's body;
a positioning processor operatively connected to the catheter for determining positional information of the portion of the catheter based on the electrical signals transmitted by the position sensor;
a display; and
an image processor operatively connected to the catheter, the positioning processor and the display, the image processor registering the pre-acquired image with the ultrasonic image transmitted by the ultrasonic sensor and depicting the ultrasonic image on the three-dimensional model on the display in real-time in a same orientation as an orientation of the portion of the catheter in the patient's body based on positional information derived from the position sensor.

An alternative embodiment of the present invention is a medical imaging system for imaging a target in a patient's body wherein the system comprises:

a pre-acquired image;
a catheter comprising a position sensor and an ultrasonic imaging sensor, the position sensor transmitting electrical signals indicative of positional information of a portion of the catheter in a patient's body and the ultrasonic imaging sensor transmitting ultrasonic energy at a target in the patient's body, receiving ultrasonic echoes reflected from the target in the patient's body and transmitting signals relating to the ultrasonic echoes reflected from the target in the patient's body;

a positioning processor operatively connected to the catheter for determining positional information of the portion of the catheter based on the electrical signals transmitted by the position sensor;

a display; and an image processor operatively connected to the catheter, the positioning processor and the display, the image processor generating at least one two-dimensional ultrasonic image of the target based on the signals transmitted by the ultrasonic sensor and reconstructing a three-dimensional model using the at least one two-dimensional ultrasonic image and registering the pre-acquired image with the three-dimensional model and depicting a real-time two-dimensional ultrasonic image on the registered pre-acquired image and three-dimensional model on the display in a same orientation as an orientation of the portion of the catheter in the patient's body based on positional information derived from the position sensor.

Moreover, an alternative embodiment of the present invention is a medical imaging system for imaging a patient's body, wherein the system comprises:

a catheter comprising a position sensor and an ultrasonic imaging sensor, the position sensor transmitting electrical signals indicative of positional information of a portion of the catheter in a patient's body and the ultrasonic imaging sensor transmitting ultrasonic energy at a target in the patient's body, receiving ultrasonic echoes reflected from the target in the patient's body and transmitting signals relating to the ultrasonic echoes reflected from the target in the patient's body;

a positioning processor operatively connected to the catheter for determining positional information of the portion of the catheter based on the electrical signals transmitted by the position sensor;

a display; and an image processor operatively connected to the catheter, the positioning processor and the display, the image processor displaying on the display a catheter icon in a same orientation as an orientation of the portion of the catheter in the patient's body based on positional information derived from the position sensor, the image processor also generating an ultrasonic image of the target based on the signals transmitted by the ultrasonic sensor and depicting in real-time the generated ultrasound image on a display in a same orientation as the orientation of the portion of the catheter in the patient's body based on positional information derived from the position sensor. The catheter icon is used for directing the transmitted ultrasonic energy at a target in the patient's body from the ultrasonic sensor of the catheter in a particular direction.

The present invention will be more fully understood from the following detailed description of the embodiments thereof, taken together with the drawings in which:

DETAILED DESCRIPTION OF EMBODIMENTS

System Description

Figure 1:
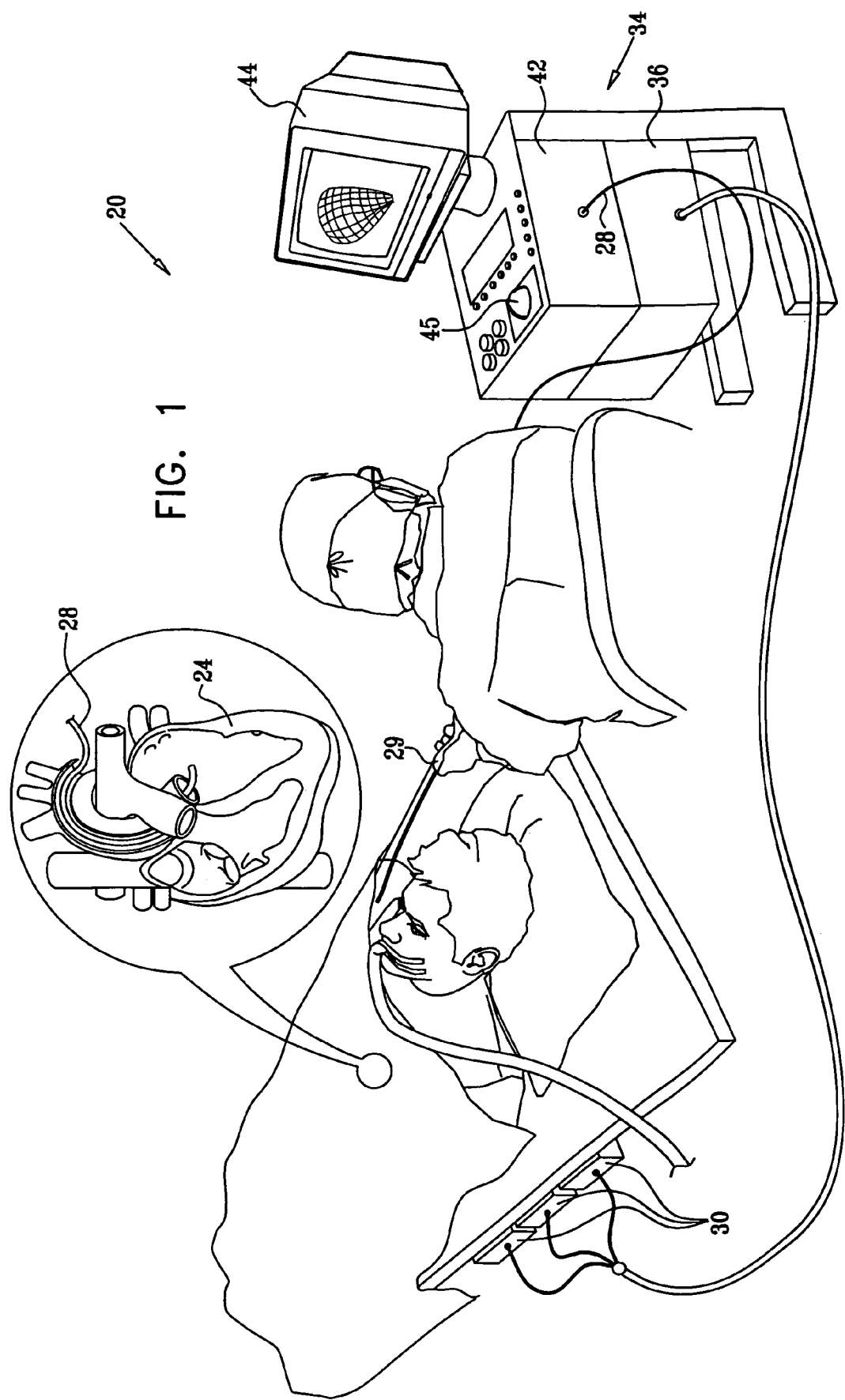
FIG. 1 is a schematic, pictorial illustration of a system for cardiac mapping and imaging, in accordance with an embodiment of the present invention.

FIG. 1 is a schematic, pictorial illustration of a system 20 for imaging and mapping a heart 24 of a patient, in accordance with an embodiment of the present invention. The system comprises a catheter 28, which is inserted by a physician into a chamber of the heart through a vein or artery. Catheter 28 typically comprises a handle 29 for operation of the catheter by the physician. Suitable controls on the handle enable the physician to steer, position and orient the distal end of the catheter as desired.

System 20 comprises a positioning sub-system that measures location and orientation coordinates of catheter 28. (Throughout this patent application, the term "location" refers to the spatial coordinates of the catheter, and the term "orientation" refers to its angular coordinates. The term "position" refers to the full positional information of the catheter, comprising both location and orientation coordinates.)

In one embodiment, the positioning sub-system comprises a magnetic position tracking system that determines the position and orientation of catheter 28. The positioning sub-system generates magnetic fields in a predefined working volume its vicinity and senses these fields at the catheter. The positioning sub-system typically comprises a set of external radiators, such as field generating coils 30, which are located in fixed, known positions external to the patient. Coils 30 generate fields, typically electromagnetic fields, in the vicinity of heart 24. The generated fields are sensed by a position sensor 32 inside catheter 28.

In an alternative embodiment, a radiator, such as a coil, in the catheter generates electromagnetic fields, which are received by sensors outside the patient's body.

The position sensor transmits, in response to the sensed fields, position-related electrical signals over cables 33 running through the catheter to a console 34. Alternatively, the position sensor may transmit signals to the console over a wireless link. The console comprises a positioning processor 36 that calculates the location and orientation of catheter 28 based on the signals sent by position sensor 32. Positioning processor 36 typically receives, amplifies, filters, digitizes, and otherwise processes signals from catheter 28.

Some position tracking systems that may be used for this purpose are described, for example, in U.S. Pat. Nos. 6,690,963, 6,618,612 and 6,332,089, and U.S. Patent Application Publications 2002/0065455 A1, 2004/0147920 A1 and 2004/0068178 A1, whose disclosures are all incorporated herein by reference. Although the positioning sub-system shown in FIG. 1 uses magnetic fields, the methods described below may be implemented using any other suitable positioning sub-system, such as systems based on electromagnetic fields, acoustic or ultrasonic measurements.

Figure 10:
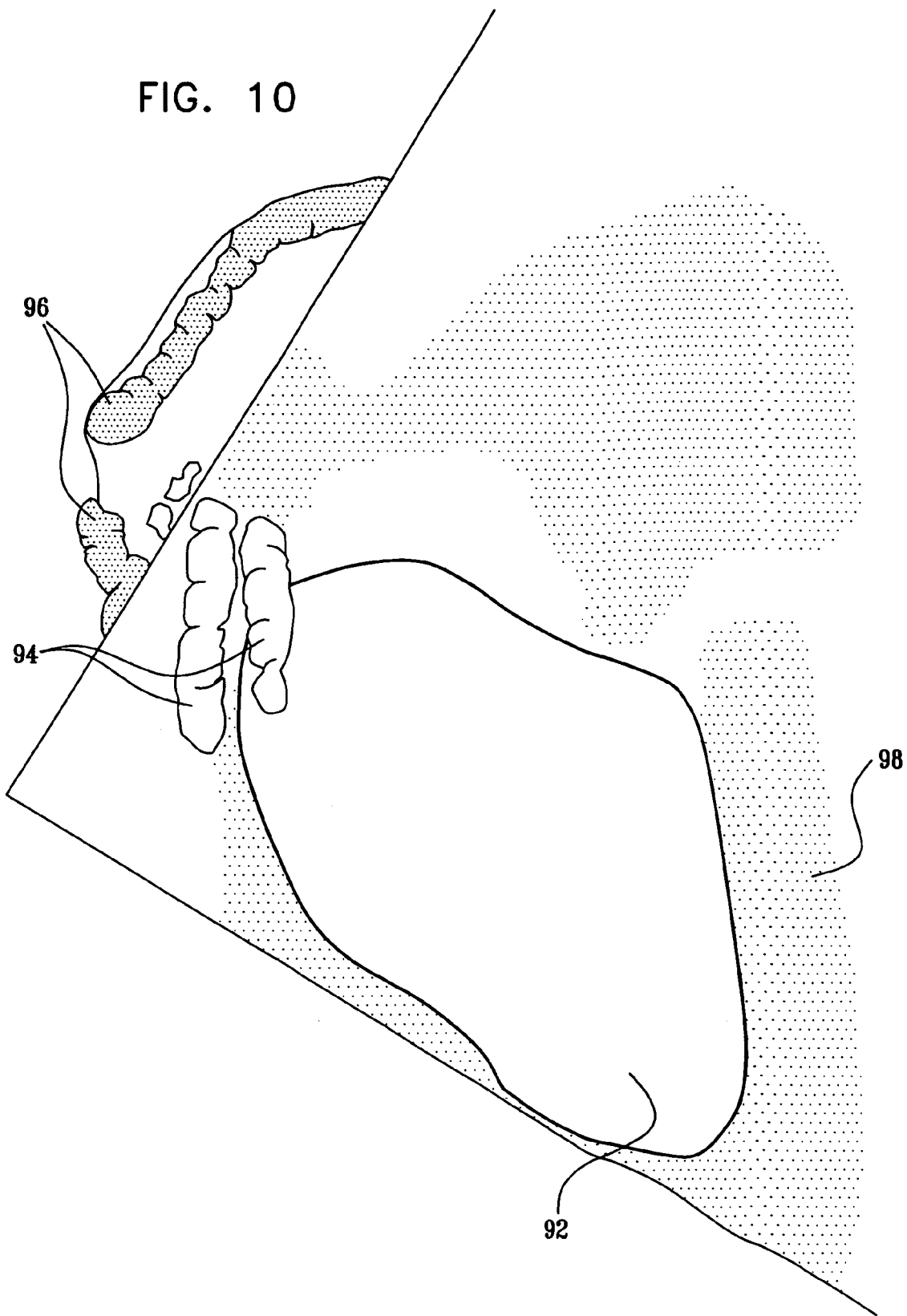
Figure 11:
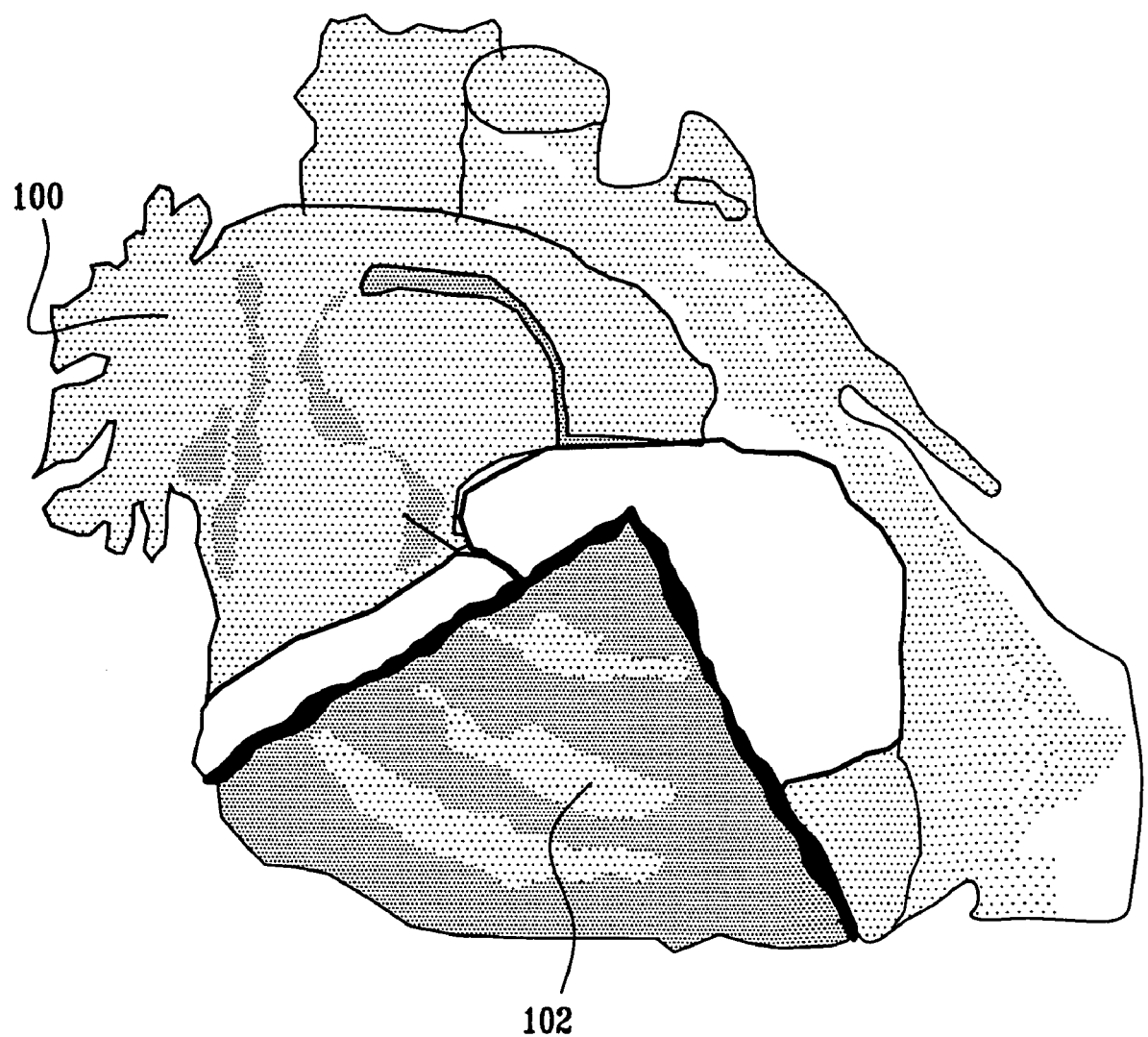
FIG. 11 is an image that visually demonstrates an ultrasound image registered with a pre-acquired image, in accordance with an embodiment of the present invention.

As will be explained and demonstrated below, system 20 enables the physician to perform a variety of mapping and imaging procedures. These procedures comprise, for example, the following:

- Display real-time or near real-time (NRT) 2-D ultrasound images (See FIGS. 4 and 6 below).
- Reconstruct 3-D models of a target structure in the patient's body, based on 2-D ultrasound images (See FIGS. 4-10 below).
- Register, overlay and display a parametric map, such as an electro-physiological information map or an electro-anatomical map on the reconstructed 3-D model (See FIG. 8 below).
- Register, overlay and display a 3-D image acquired from an external system on the reconstructed 3-D model.
- Register and display 2-D ultrasound images on a 3-D image acquired from an external system (See FIG. 11 below).

Figure 2:
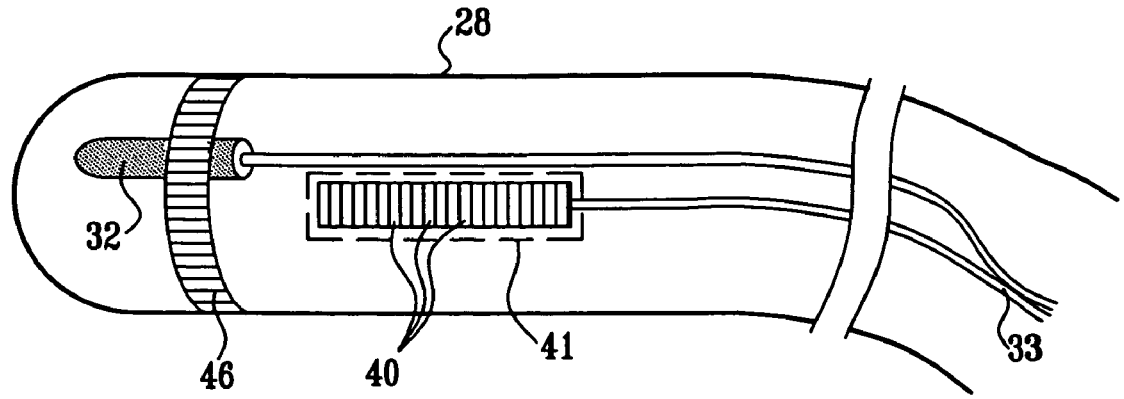
FIG. 2 is a schematic, pictorial illustration of a catheter, in accordance with an embodiment of the present invention.

FIG. 2 is a schematic, pictorial illustration that shows the distal end of catheter 28, in accordance with an embodiment of the present invention. The catheter comprises an ultrasonic imaging sensor. The ultrasonic sensor typically comprises an array of ultrasonic transducers 40. In one embodiment, the transducers are piezo-electric transducers. The ultrasonic transducers are positioned in or adjacent to a window 41, which defines an opening within the body or wall of the catheter.

Transducers 40 operate as a phased array, jointly transmitting an ultrasound beam from the array aperture through window 23. (Although the transducers are shown arranged in a linear array configuration, other array configurations can be used, such as circular or convex configurations.) In one embodiment, the array transmits a short burst of ultrasound energy and then switches to a receiving mode for receiving the ultrasound signals reflected from the surrounding tissue. Typically, transducers 40 are driven individually in a controlled manner in order to steer the ultrasound beam in a desired direction. By appropriate timing of the transducers, the produced ultrasound beam can be given a concentrically curved wave front, so as to focus the beam at a given distance from the transducer array. Thus, system 20 uses the transducer array as a phased array and implements a transmit/receive scanning mechanism that enables the steering and focusing of the ultrasound beam, so as to produce 2-D ultrasound images.

In one embodiment, the ultrasonic sensor comprises between sixteen and sixty-four transducers 40, preferably between forty-eight and sixty-four transducers. Typically, the transducers generate the ultrasound energy at a center frequency in the range of 5-10 MHz, with a typical penetration depth of 14 cm. The penetration depth typically ranges from several millimeters to around 16 centimeters, and depends upon the ultrasonic sensor characteristics, the characteristics of the surrounding tissue and the operating frequency. In alternative embodiments, other suitable frequency ranges and penetration depths can be used.

After receiving the reflected ultrasound echoes, electric signals based on the reflected echoes are sent by transducers 40 over cables 33 through catheter 28 to an image processor 42 in console 34, which transforms them into 2-D, typically sector-shaped ultrasound images. Image processor 42 typically computes or determines position and orientation information, displays real-time ultrasound images, performs 3-D image or volume reconstructions and other functions which will all be described in greater detail below.

In some embodiments, the image processor uses the ultrasound images and the positional information to produce a 3-D model of a target structure of the patient's heart. The 3-D model is presented to the physician as a 2-D projection on a display 44.

In some embodiments, the distal end of the catheter also comprises at least one electrode 46 for performing diagnostic and/or therapeutic functions, such as electro-physiological mapping and/or radio frequency (RF) ablation. In one embodiment, electrode 46 is used for sensing local electrical potentials. The electrical potentials measured by electrode 46 may be used in mapping the local electrical activity on the endocardial surface. When electrode 46 is brought into contact or proximity with a point on the inner surface of the heart, it measures the local electrical potential at that point. The measured potentials are converted into electrical signals and sent through the catheter to the image processor for display. In other embodiments, the local electrical potentials are obtained from another catheter comprising suitable electrodes and a position sensor, all connected to console 34.

In alternative embodiments, electrode 46 can be used to measure different parameters, such as various tissue characteristics, temperature and/or blood flow. Although electrode 46 is shown as being a single ring electrode, the catheter may comprise any number of electrodes 46 in any form. For example, the catheter may comprise two or more ring electrodes, a plurality or array of point electrodes, a tip electrode, or any combination of these types of electrodes for performing the diagnostic and/or therapeutic functions outlined above.

Position sensor 32 is typically located within the distal end of catheter 28, adjacent to electrode 46 and transducers 40. Typically, the mutual positional and orientational offsets between position sensor 32, electrode 46 and transducers 40 of the ultrasonic sensor are constant. These offsets are typically used by positioning processor 36 to derive the coordinates of the ultrasonic sensor and of electrode 46, given the measured position of position sensor 32. In another embodiment, catheter 28 comprises two or more position sensors 32, each having constant positional and orientational offsets with respect to electrode 46 and transducers 40. In some embodiments, the offsets (or equivalent calibration parameters) are pre-calibrated and stored in positioning processor 36. Alternatively, the offsets can be stored in a memory device (such as an electrically-programmable read-only memory, or EPROM) fitted into handle 29 of catheter 28.

Position sensor 32 typically comprises three non-concentric coils (not shown), such as described in U.S. Pat. No. 6,690,963 cited above. Alternatively, any other suitable position sensor arrangement can be used, such as sensors comprising any number of concentric or non-concentric coils, Hall-effect sensors and/or magneto-resistive sensors.

Typically, both the ultrasound images and the position measurements are synchronized with the heart cycle, by gating signal and image capture relative to a body-surface electrocardiogram (ECG) signal or intra-cardiac electrocardiogram. (In one embodiment, the ECG signal can be produced by electrode 46.) Since features of the heart change their shape and position during the heart's periodic contraction and relaxation, the entire imaging process is typically performed at a particular timing with respect to this period. In some embodiments, additional measurements taken by the catheter, such as measurements of various tissue characteristics, temperature and blood flow measurements, are also synchronized to the electrocardiogram (ECG) signal. These measurements are also associated with corresponding position measurements taken by position sensor 32. The additional measurements are typically overlaid on the reconstructed 3-D model, as will be explained below.

In some embodiments, the position measurements and the acquisition of the ultrasound images are synchronized to an internally-generated signal produced by system 20. For example, the synchronization mechanism can be used to avoid interference in the ultrasound images caused by a certain signal. In this example, the timing of image acquisition and position measurement is set to a particular offset with respect to the interfering signal, so that images are acquired without interference. The offset can be adjusted occasionally to maintain interference-free image acquisition. Alternatively, the measurement and acquisition can be synchronized to an externally-supplied synchronization signal.

In one embodiment, system 20 comprises an ultrasound driver (not shown) that drives the ultrasound transducers 40. One example of a suitable ultrasound driver, which can be used for this purpose is an AN2300™ ultrasound system produced by Analogic Corp. (Peabody, Mass.). In this embodiment, the ultrasound driver performs some of the functions of image processor 42, driving the ultrasonic sensor and producing the 2-D ultrasound images. The ultrasound driver may support different imaging modes such as B-mode, M-mode, CW Doppler and color flow Doppler, as are known in the art.

Typically, the positioning and image processors are implemented using a general-purpose computer, which is programmed in software to carry out the functions described herein. The software may be downloaded to the computer in electronic form, over a network, for example, or it may alternatively be supplied to the computer on tangible media, such as CD-ROM. The positioning processor and image processor may be implemented using separate computers or using a single computer, or may be integrated with other computing functions of system 20. Additionally or alternatively, at least some of the positioning and image processing functions may be performed using dedicated hardware.

3-D Imaging Method

Figure 3:
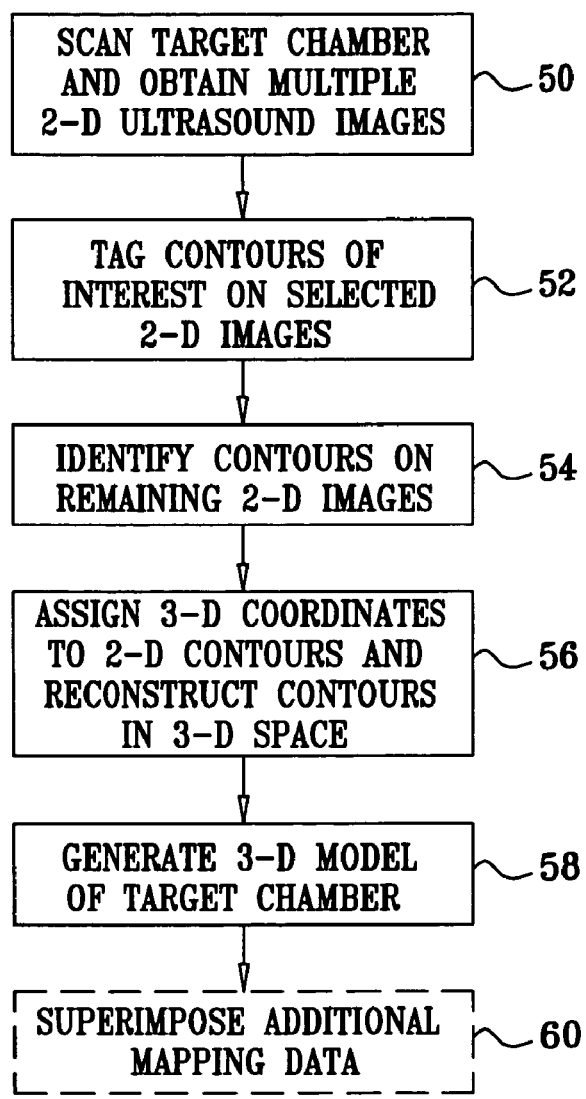
FIG. 3 is a flow chart that schematically illustrates a method for cardiac mapping and imaging, in accordance with an embodiment of the present invention.

FIG. 3 is a flow chart that schematically illustrates a method for cardiac mapping and imaging, in accordance with an embodiment of the present invention. In principle, the disclosed method combines multiple 2-D ultrasound images, acquired at different positions of the catheter, into a single 3-D model of the target structure. In the context of the present patent application and in the claims, the term "target structure" or "target" may refer to a chamber of the heart, in whole or in part, or to a particular wall, surface, blood vessel or other anatomical feature. Although the embodiments described herein refer particularly to structures in and around the heart, the principles of the present invention may similarly be applied, mutatis mutandis, in imaging of bones, muscles and other organs and anatomical structures.

The method begins with acquisition of a sequence of 2-D ultrasound images of the target structure, at an ultrasound scanning step 50. Typically, the physician inserts catheter 28 through a suitable blood vessel into a chamber of the heart, such as the right atrium, and then scans the target structure by moving the catheter between different positions inside the chamber. The target structure may comprise all or a part of the chamber in which the catheter is located or, additionally or alternatively, a different chamber, such as the left atrium, or vascular structures, such as the aorta. In each catheter position, the image processor acquires and produces a 2-D ultrasound image, such as the image shown in FIG. 4 below.

In parallel, the positioning sub-system measures and calculates the position of the catheter. The calculated position is stored together with the corresponding ultrasound image. Typically, each position of the catheter is represented in coordinate form, such as a six-dimensional coordinate (X, Y, Z axis positions and pitch, yaw and roll angular orientations).

In some embodiments, the catheter performs additional measurements using electrode 46. The measured parameters, such as local electrical potentials, are optionally overlaid and displayed as an additional layer on the reconstructed 3-D model of the target structure, as will be explained below.

Figure 5:
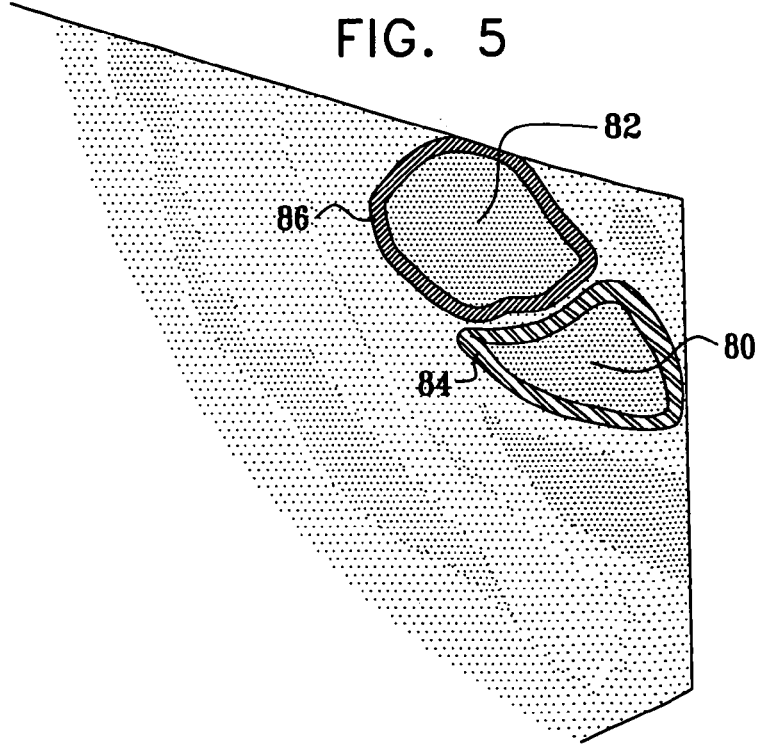

After obtaining the set of ultrasound images, the image processor displays one or more of these images to the physician, at a manual tagging step 52. Alternatively, step 52 may be interleaved with step 50. The gray levels in the images enable the physician to identify structures, such as the walls of heart chambers, blood vessels and valves. The physician examines the ultrasound images and identifies contours-of-interest that represent walls or boundaries of the target structure. The physician marks the contours on display 44, typically by "tagging" them using a pointing device 45, such as a track-ball. (An exemplary tagged 2-D image is shown in FIG. 5 below.) The pointing device may alternatively comprise a mouse, a touch-sensitive screen or tablet coupled to display 44, or any other suitable input device. The combination of display 44 and pointing device 45 is an example of an interactive display, i.e., means for presenting an image and permitting the user to mark on the image in such a way that a computer is able to locate the marks in the image. Other types of interactive displays will be apparent to those skilled in the art.

The physician may tag the contours on one or several images out of the set in this manner. The physician may also tag various anatomical landmarks or artifacts, as relevant to the medical procedure in question. The physician may similarly identify "keep away" areas that should not be touched or entered in a subsequent therapeutic procedure, such as ablation.

In some embodiments, the contours-of-interest are tagged in a semi-automatic manner. For example, the image processor may run suitable contour detection software. In this embodiment, the software automatically detects and marks contours in one or more of the 2-D images. The physician then reviews and edits the automatically-detected contours using the interactive display.

The image processor may use the tagged contours to automatically reconstruct the contours in the remaining, untagged ultrasound images, at an automatic tagging step 54. (In some embodiments, the physician may tag all 2-D ultrasound images at step 52. In this case, step 54 is omitted.) The image processor traces the structures tagged by the physician, and reconstructs them in the remaining ultrasound images. This identification and reconstruction process may use any suitable image processing method, including edge detection methods, correlation methods, motion detection methods and other methods known in the art. The position coordinates of the catheter that are associated with each of the images may also be used by the image processor in correlating the contour locations from image to image. Additionally or alternatively, step 54 may be implemented in a user-assisted manner, in which the physician reviews and corrects the automatic contour reconstruction carried out by the image processor. The output of step 54 is a set of 2-D ultrasound images, tagged with the contours-of-interest.

The image processor subsequently assigns 3-D coordinates to the contours-of-interest identified in the set of images, at a 3-D coordinate assignment step 56. Although in step 52 the physician marks the tags on 2-D images, the location and orientation of the planes of these images in 3-D space are known by virtue of the positional information, stored together with the images at step 50. Therefore, the image processor is able to determine the 3-D coordinates for each pixel or of any pixel in the 2-D images, and in particular those corresponding to the tagged contours. When assigning the coordinates, the image processor typically uses the stored calibration data comprising the position and orientation offsets between the position sensor and the ultrasonic sensor, as described above.

In some embodiments, the contours-of-interest comprise discrete points. In these embodiments, the positioning processor assigns a 3-D coordinate to each such discrete point. Additionally, the positioning processor assigns a 3-D coordinate to discrete points of a surface or a volume (defined by surfaces) such as a chamber of a heart. Thus, registration of the pre-acquired image to the one or more 2-D ultrasound images or 3-D model of the ultrasound images can be performed using contours, discrete points, surfaces or volumes.

In some embodiments, the image processor displays one or more of the 2-D ultrasound images, appropriately oriented in 3-D space. (See, for example, FIG. 6 below.) The contours-of-interest may optionally be marked on the oriented 2-D image.

The image processor produces a 3-D skeleton model of the target structure, at a 3-D reconstruction step 58. The image processor arranges the tagged contours from some or all of the 2-D images in 3-D space to form the skeleton model. (See an exemplary skeleton model in FIG. 7 below.) In some embodiments, the image processor uses a "wire-mesh" type process to generate surfaces over the skeleton model and produce a solid 3-D shape of the target structure. The image processor projects the contours-of-interest on the generated 3-D model. The model is typically presented to the physician on display 44. (See exemplary 3-D models in FIGS. 8-10 below.)

As described above, in some embodiments system 20 supports a measurement of local electrical potentials on the surfaces of the target structure. In this measurement, each electrical activity data-point acquired by catheter 28 comprises an electrical potential or activation time value measured by electrode 46 and the corresponding position coordinates of the catheter measured by the positioning sub-system for creation or generation of an electrophysiological map (by the image processor). The image processor registers the electrical activity data-points with the coordinate system of the 3-D model and overlays them on the model, at an overlaying step 60. Step 60 is optional in the method and is performed only if system 20 supports this type of measurement and if the physician has chosen to use this feature. The electrical activity data-points are typically measured when electrode 46 is in contact with, or in close proximity to, the wall of the target structure. Therefore, the data-points are typically superimposed on the 3-D model of the structure.

Alternatively, a separate 3-D electrical activity map (often referred to as an electro-anatomical map) can be generated and displayed. For example, a suitable electro-anatomical map can be produced by a CARTO™ navigation and mapping system, manufactured and sold by Biosense Webster, Inc. (Diamond Bar, Calif.). The electrical potential values may be presented using a color scale, for example, or any other suitable visualization method. In some embodiments, the image processor may interpolate or extrapolate the measured electrical potential values and display a full color map that describes the potential distribution across the walls of the target structure. As defined herein, the term "electrophysiological map" means a map of electrical activity data-points or an electro-anatomical map.

As noted above, information imported from other imaging applications may be registered with the 3-D model and over-laid on the model for display. For example, pre-acquired computerized tomography (CT), magnetic resonance imaging (MRI) or x-ray information may be registered with the 3-D ultrasound-based model and displayed together with the 3-D model and/or with 2-D ultrasound images on display 44. (See an exemplary overlay of a 2-D image and a pre-acquired CT image in FIG. 11 below.)

Additionally or alternatively, if additional parametric measurements were taken at step 50 above, these measurements can be registered with the 3-D model and displayed as an additional layer (often referred to as a "parametric map.")

When implementing the disclosed method, the order of steps 50-60 may be modified, and steps may be repeated in an interactive manner. For example, the physician may acquire a first sequence 2-D images and tag them manually. Then, the physician may go back and acquire additional images and have the system tag them automatically, using the tagged contours in the first sequence of images. The physician may then generate the full 3-D model and examine it. If the model is not accurate enough in some areas, the physician may decide to acquire an additional set of images in order to refine the 3-D model. Additionally or alternatively, the physician may decide, after examining the images or the 3-D model, to change the manual tagging of one or more of the images, or to override the automatic tagging process. Other sequences of applying steps 50-60, in order to reach a high quality 3-D model of the target structure, may also be followed by the physician. Additionally or alternatively, some of these steps may be carried out automatically, under robotic control, for example.

In some embodiments, features from the 2-D ultrasound images are selectively displayed as part of the 3-D model. For example, features that are located outside the volume defined by the contours-of-interest may be discarded or hidden from the displayed model. Alternatively or additionally, only the skeleton model or the wire-mesh model can be displayed. Other suitable criteria can be used for filtering the information to be displayed. For example, "keep away" areas marked in one or more of the 2-D images, as described above, may be suitably drawn and highlighted in the 3-D model.

In some embodiments, system 20 can be used as a real-time or near real-time imaging system. For example, the physician can reconstruct a 3-D model of the target structure using the methods described above, as a preparatory step before beginning a medical procedure. The physician can tag any desired anatomical landmarks or features of interest, which are displayed on the 3-D model. During the procedure, system 20 can continuously track and display the 3-D position of the catheter with respect to the model and the tagged contours. The catheter used for performing the medical procedure may be the same catheter used for generating the 3-D model, or a different catheter fitted with a suitable position sensor.

Cardiac Imaging Example

FIGS. 4-8 are images that visually demonstrate the 3-D imaging method described above, in accordance with an embodiment of the present invention. The figures were produced from ultrasound images generated by a cardiac imaging system implemented by the inventors. The images were produced during a real-life experiment that imaged the heart of a pig using a catheter similar to the catheter shown in FIG. 2 above.

Figure 4:
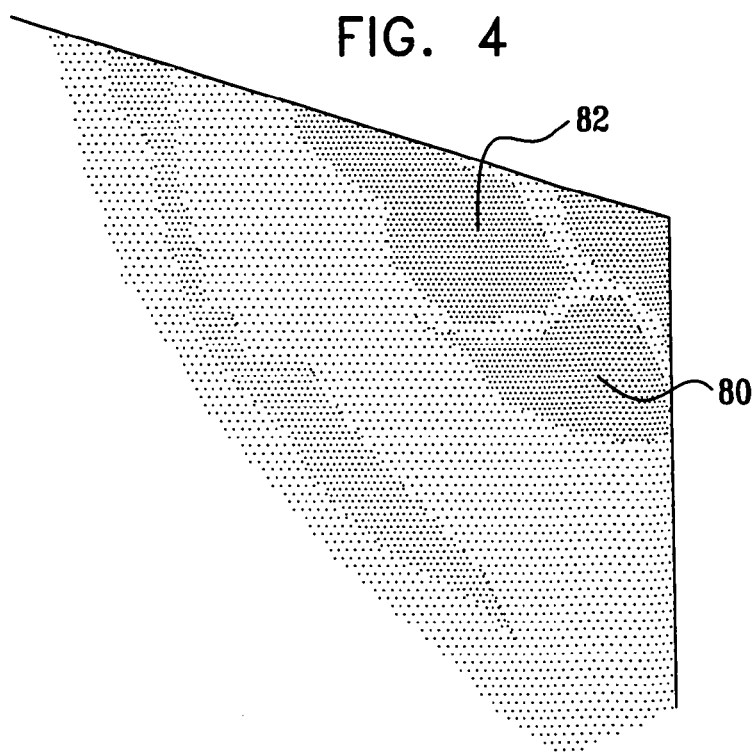
FIGS. 4-8 are images that visually demonstrate a method for cardiac mapping and imaging, in accordance with an embodiment of the present invention.

FIG. 4 shows a 2-D ultrasound image acquired by the ultrasonic transducers at a particular position of catheter 28. The image shows two distinct features 80 and 82 of the heart. Multiple ultrasound images of this form were acquired at different positions of the catheter, in accordance with ultrasound scanning step 50 of the method of FIG. 3 above.

FIG. 5 shows the ultrasound image of FIG. 4, with features 80 and 82 marked with contours 84 and 86, respectively. FIG. 4 was taken with the catheter positioned in the right atrium. In this 2-D ultrasound image, feature 80 represents the mitral valve and feature 82 represent the aortic valve. The contours were manually tagged by a user, in accordance with manual tagging step 52 of the method of FIG. 3 above. Contours 84 and 86 mark the anatomical structures in the 3-D working volume and assist the physician to identify these structures during the procedure.

Figure 6:
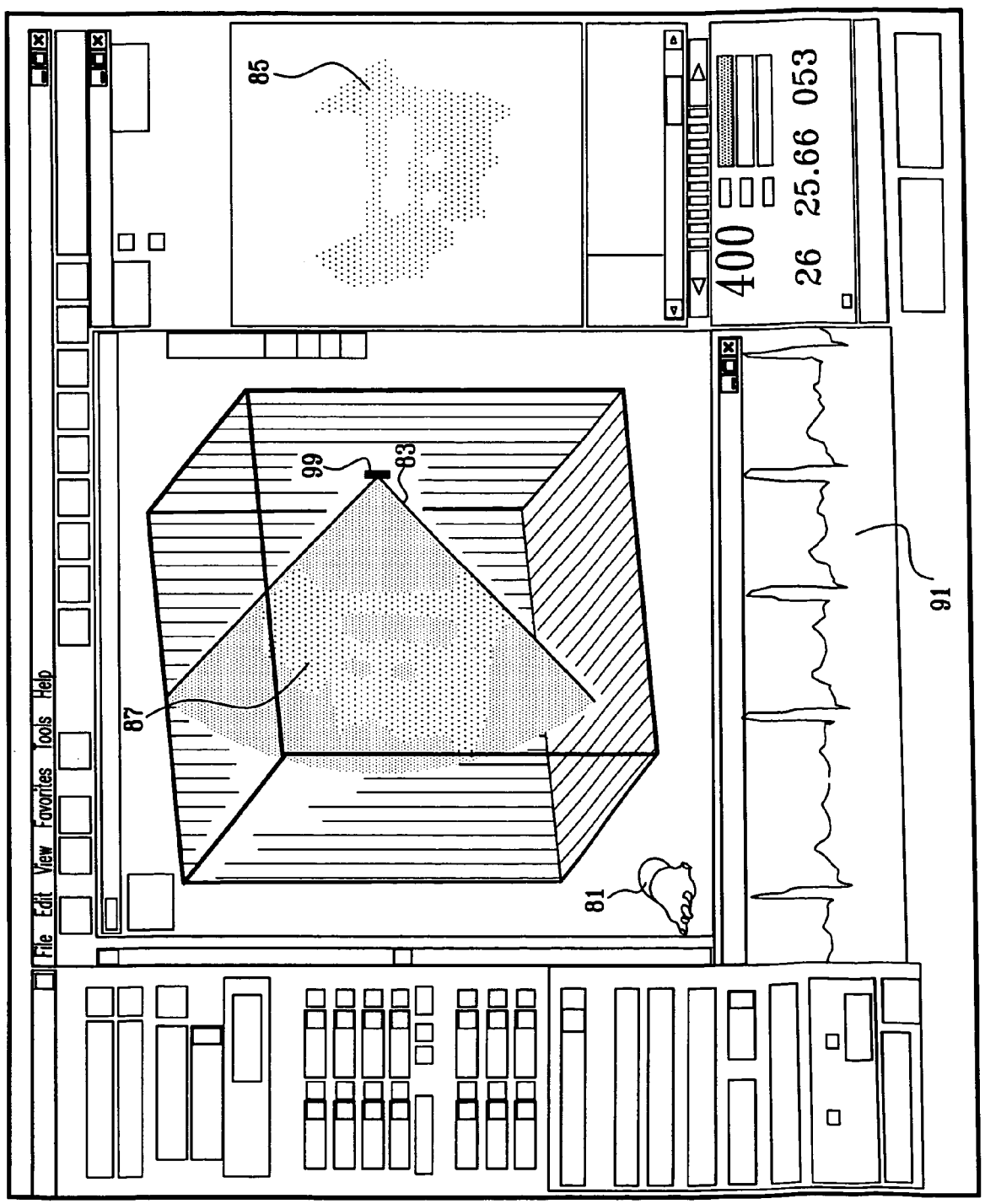

FIG. 6 shows a 2-D ultrasound image 85 oriented and projected in 3-D space. The figure shows an exemplary split-screen display, as can be produced by image processor 42 and displayed on display 44 of system 20. The "raw" 2-D image is displayed in a separate window on the right hand side of the figure.

An isometric display at the center of the figure shows a projected image 87, produced by orienting and projecting the plane of image 85 in 3-D space, in accordance with the position measurement of position sensor 32. An orientation icon 81, typically having the shape of the imaged anatomical structure (a heart in this example), is displayed with the same orientation as projected image 87 in real-time as catheter 28 is moved within the patient's body. Icon 81 assists the physician in understanding the 3-D orientation of the projected image.

A beam icon 83 is used in association with projected 2-D image 87 to mark the area scanned by the ultrasound beam. As such, icon 83 is oriented and displayed in the same plane (same orientation) as projected image 87 in real-time as catheter 28 is moved within the patient's body. Icon 83 may comprise a web-like or fan-like linear depiction, preferably in color, such as red. Alternatively, icon 83 may comprise a colored line marking the perimeter of the area scanned by the beam to produce image 87, or any other suitable means for visualizing the position and orientation of the ultrasound beam. In the example of FIG. 6, icon 83 comprises two straight lines indicating the angular sector defined by the ultrasound beam. In some embodiments, an additional icon 99 marking the location and position of the distal end of catheter 28 is also displayed. For example, the distal end of catheter 28 is displayed as a catheter tip icon 99 that permits the physician or user of system 20 to understand the location and orientation of ultrasound images captured by the catheter 28, independently of whether any other image processing is used to orient the 2-D ultrasound image or fan 87 or to superimpose the 2-D image on a 3-D image or frame. The physician or user of suystem 20 may also use the icon 99 for aiming or directing the ultrasound beam in a desired direction and/orientation. For example, the catheter tip icon 99 may be used in positioning the tip of catheter 28 adjacent to a known landmark in the heart in order to facilitate a more accurate estimation of the direction of the ultrasound beam.

Projected image 87 is typically displayed inside a cube that marks the boundaries of the working volume. The working volume is typically referenced to the coordinate system of field radiating coils 30 of the positioning sub-system shown in FIG. 1 above. In one embodiment, each side of the cube (i.e., the characteristic dimension of the working volume) measures approximately 12 cm. Alternatively, any other suitable size and shape can be chosen for the working volume, typically depending upon the tissue penetration capability of the ultrasound beam.

A signal display 91 at the bottom of the figure shows the ECG signal, to which the measurements are synchronized, as explained above.

When system 20 operates in real time, the position and orientation of the projected image and of icon 83 change with the movements of catheter 28. In some embodiments, the physician can change the angle of observation, zoom in and out and otherwise manipulate the displayed images using the interactive display. The user interface features described herein are shown as an exemplary configuration. Any other suitable user interface can be used.

In some embodiments, system 20 and the associated user interface can be used for 3-D display and projection of 2-D ultrasound images, without reconstructing a 3-D model. For example, the physician can acquire a single 2-D ultrasound image and tag contours-of-interest on this image. System 20 can then orient and project the ultrasound image in 3-D space, in a manner similar to the presentation of projected image 87. If desired, during the medical procedure the system can continuously track and display the 3-D position of the catheter performing the procedure (which may be different from the catheter acquiring image 87) with respect to the projected ultrasound image and the tagged contours.

Figure 7:
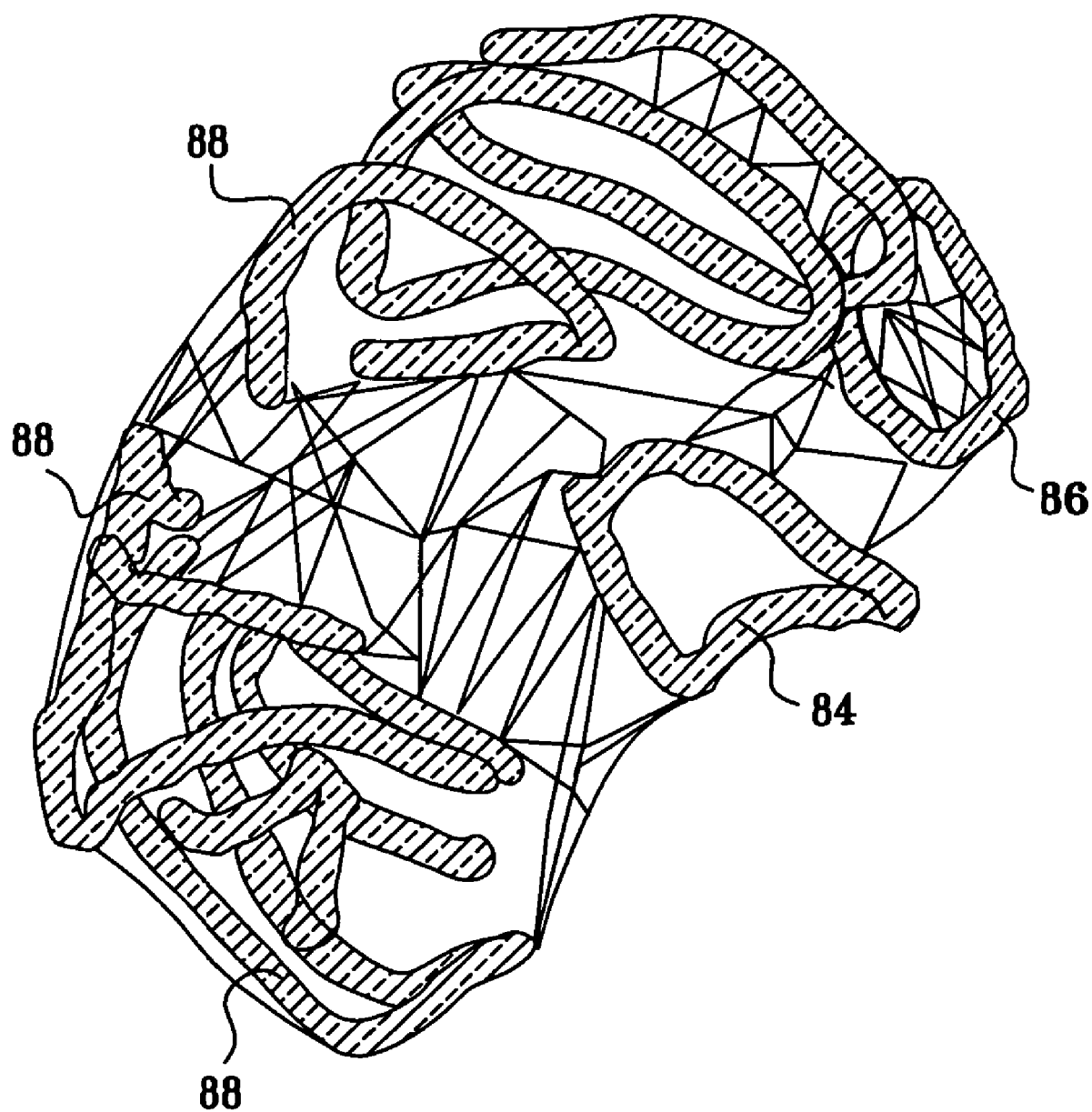

FIG. 7 shows a skeleton model of the target structure, in this example comprising the right ventricle, produced by the image processor in accordance with 3-D reconstruction step 58 of the method of FIG. 3 above. Prior to generating the skeleton model, the image processor traced and reconstructed contours 84 and 86 in the untagged ultrasound images, in accordance with automatic tagging step 54. FIG. 7 shows the original contours 84 and 86 projected onto 3-D space. Contours 88 were automatically reconstructed by the image processor from other contours tagged by the physician.

Figure 8:
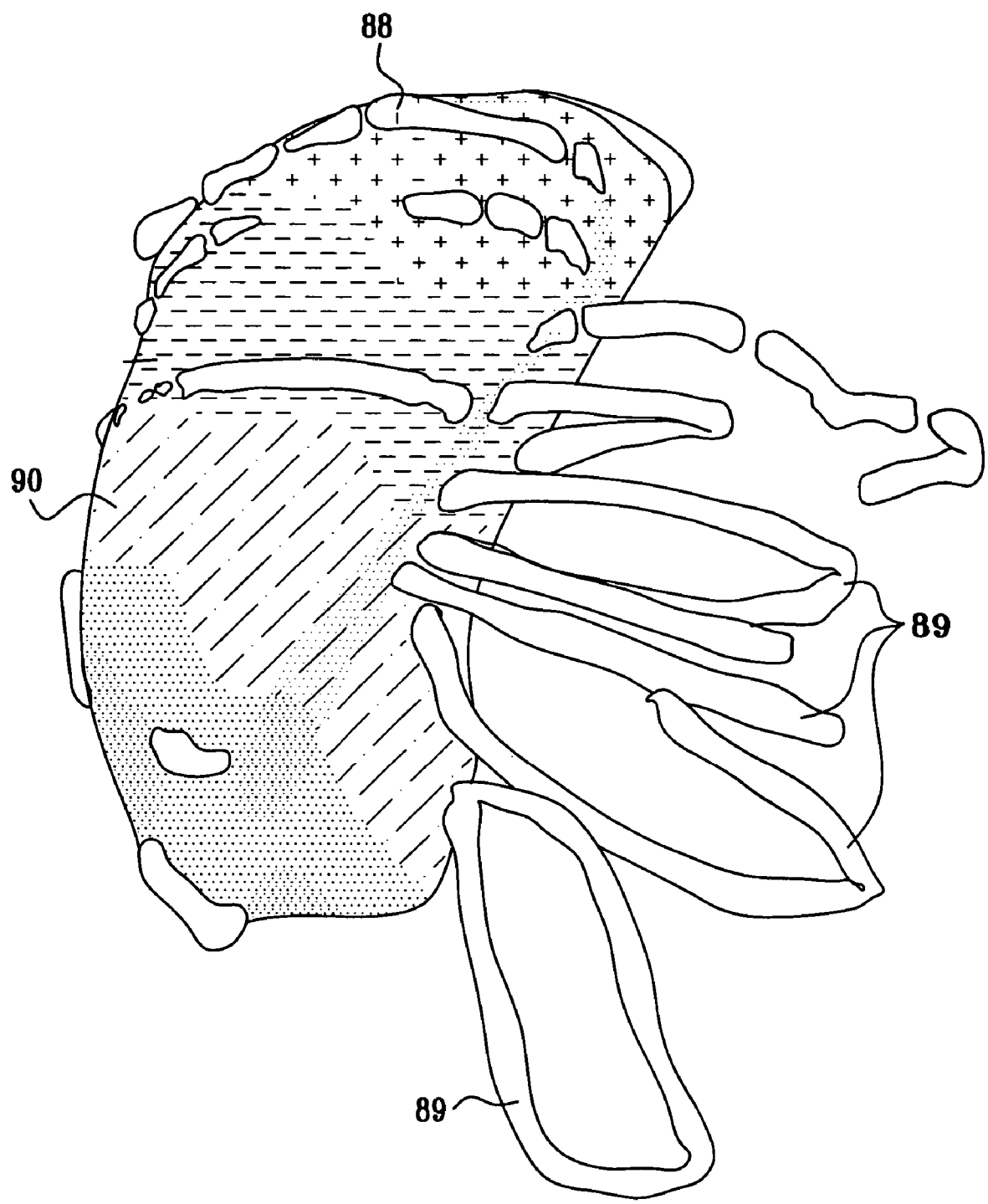

FIG. 8 shows a solid 3-D model of the right ventricle, generated by the image processor. Some of contours 88 are overlaid on the solid model. In addition, contours 89 showing the left ventricle can also be seen in the figure. The surface of the right ventricle is overlaid with an electrical activity map 90, as measured by electrode 46 in accordance with overlaying step 60 of the method of FIG. 3 above. The map presents different electrical potential values using different colors (shown as different shading patterns in FIG. 8).

Figure 9:
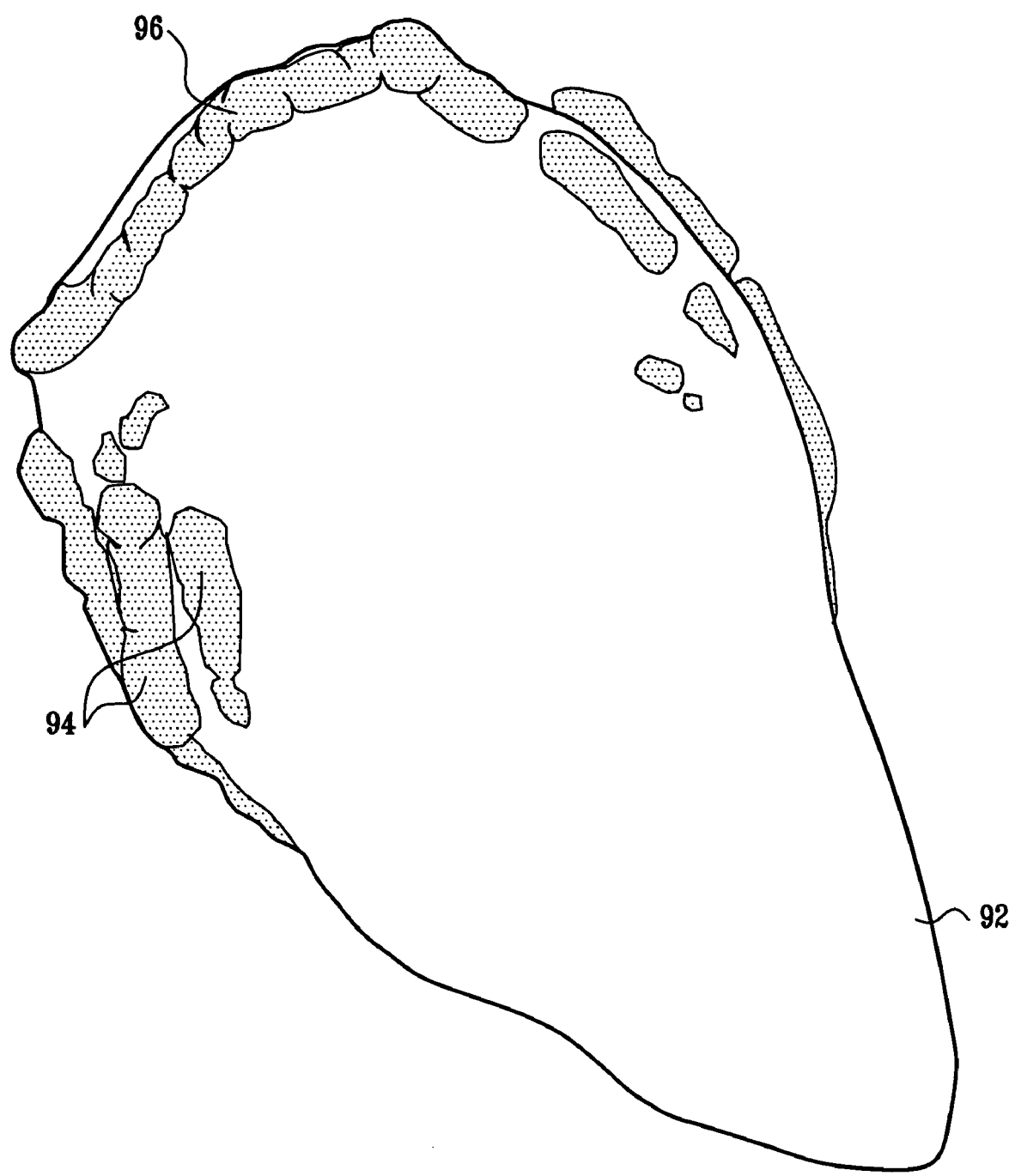
FIGS. 9 and 10 are images that visually demonstrate a modeled cardiac chamber, in accordance with an embodiment of the present invention.

FIGS. 9 and 10 are images that visually demonstrate modeled left atria, in accordance with an embodiment of the present invention. In both figures, the atrium is shown as a solid model 92. A contour 94 tagged by the physician marks the location of the fossa ovalis. Contours 96 mark additional contours of interest used to construct solid model 92. In FIG. 10, a 2-D ultrasound image 98 is registered with the coordinate system of model 92 and displayed together with the model.

FIG. 11 is an image that visually demonstrates an ultrasound image 102 registered with a pre-acquired image 100, in accordance with an embodiment of the present invention. In this example, a pre-acquired CT image is registered with the coordinate system of the 3-D model. The pre-acquired image and the 2-D ultrasound image are displayed together on display 44.

Although the embodiments described above relate specifically to ultrasound imaging using an invasive probe, such as a cardiac catheter, the principles of the present invention may also be applied in reconstructing 3-D models of organs using an external or internal ultrasound probe (such as a transthoracic probe), fitted with a positioning sensor. Additionally or alternatively, as noted above, the disclosed method may be used for 3-D modeling of organs other than the heart. Further additionally or alternatively, other diagnostic or treatment information, such as tissue thickness and ablation temperature, may be overlaid on the 3-D model in the manner of the electrical activity overlay described above. The 3-D model may also be used in conjunction with other diagnostic or surgical procedures, such as ablation catheters. The 3-D model may also be used in conjunction with other procedures, such as an atrial septal defect closing procedure, spine surgery, and particularly minimally-invasive procedures.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A medical imaging system for imaging a patient's body, the system comprising:
   a catheter comprising a position sensor and an ultrasonic imaging sensor, the position sensor transmitting electrical signals indicative of positional information of a portion of the catheter in a patient's body and the ultrasonic imaging sensor transmitting ultrasonic energy at a target in the patient's body, receiving ultrasonic echoes reflected from the target in the patient's body and transmitting signals relating to the ultrasonic echoes reflected from the target in the patient's body;
   a positioning processor operatively connected to the catheter for determining positional information of the portion of the catheter based on the electrical signals transmitted by the position sensor;
   a display; and
   an image processor operatively connected to the catheter, the positioning processor and the display, the image processor being configured to generated an ultrasonic image of the target on the display based on the signals transmitted by the ultrasonic sensor, the image processor being further configured to generate on the display a catheter icon in a same orientation as an orientation of the portion of the catheter in the patient's body based on positional information derived from the position sensor, a beam icon to mark an area scanned by the ultrasonic image sensor and an orientation icon in a same orientation as the ultrasonic image of the target depicted on the display;
   wherein the image processor depicts in real-time the generated ultrasound image and the beam icon on the display in a same orientation as the orientation of the portion of the catheter in the patient's body based on positional information derived from the position sensor.

2. The system according to claim 1, wherein the catheter icon is used for directing the transmitted ultrasonic energy at a target in the patient's body from the ultrasonic sensor of the catheter in a particular direction.

3. The system according to claim 1, wherein the catheter icon is used for directing the transmitted ultrasonic energy at a target in the patient's body from the ultrasonic sensor of the catheter in a particular orientation.

4. The system according to claim 2, wherein the catheter icon is also used for directing the transmitted ultrasonic energy at a target in the patient's body from the ultrasonic sensor of the catheter in a particular orientation.

5. The system according to claim 2, wherein the orientation of the ultrasonic image is depicted on the display in real-time as the same orientation of the portion of the catheter as the catheter is moved within the patient's body.

6. The system according to claim 5, wherein the beam icon is depicted on the display in a color.

7. The system according to claim 6, wherein the beam icon is a web-like depiction.

8. The system according to claim 7, wherein the beam icon is a fan-like depiction.

9. The system according to claim 1, wherein the orientation icon comprises a shape of the target imaged with the catheter.

10. The system according to claim 9, wherein the target comprises an anatomical structure.

11. The system according to claim 2, wherein the ultrasonic image is a two-dimensional image.

* * * * *